(12) United States Patent
Chandler et al.

(10) Patent No.: US 7,445,844 B2
(45) Date of Patent: *Nov. 4, 2008

(54) PRECISION FLUORESCENTLY DYED POLYMERIC MICROPARTICLES AND METHODS OF MAKING AND USING SAME

(75) Inventors: Don J. Chandler, Austin, TX (US); Van S. Chandler, Austin, TX (US); Beth A. Lambert, Austin, TX (US); Janet J. Reber, Austin, TX (US); Stacie L. Phipps, Austin, TX (US)

(73) Assignee: Luminex Corporation, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/195,185

(22) Filed: Aug. 2, 2005

(65) Prior Publication Data

US 2005/0260676 A1  Nov. 24, 2005

Related U.S. Application Data

(63) Continuation of application No. 10/401,549, filed on Jul. 3, 2003, now Pat. No. 6,929,859, which is a continuation of application No. 09/172,174, filed on Oct. 14, 1998, now Pat. No. 6,632,526.

(60) Provisional application No. 60/085,584, filed on May 15, 1998, provisional application No. 60/061,938, filed on Oct. 14, 1997.

(51) Int. Cl.
*B32B 5/16* (2006.01)
(52) U.S. Cl. ...................................... 428/403; 427/222
(58) Field of Classification Search ................ 428/403; 8/550, 611, 638, 648; 427/222
See application file for complete search history.

(56) References Cited

U.S. PATENT DOCUMENTS 4,267,234 A  5/1981  Rembaum (Continued)

FOREIGN PATENT DOCUMENTS

CA  1248873  1/1989

(Continued)

OTHER PUBLICATIONS

European Search Report, Application No. 98953430.0, mailed Nov. 30, 2006.

(Continued)

*Primary Examiner*—H. T Le
(74) *Attorney, Agent, or Firm*—Charles D. Huston; Mollie E. Lettang; Daffer McDaniel, LLP

(57) ABSTRACT

An improved method of making a series of bead or microsphere or particle populations characterized by subtle variation in a proportion or ratio of at least two fluorescent dyes distributed within a single bead of each population is provided. These beads, when excited by a single excitation light source are capable of giving off several fluorescent signals simultaneously. A set containing as many as 64 distinct populations of multicolored, fluorescent beads is provided and when combined with analytical reagents bound to the surface of such beads is extremely useful for multiplexed analysis of a plurality of analytes in a single sample. Thus, methods of staining polymeric particles, the particles themselves, and methods of using such particles are claimed.

52 Claims, 6 Drawing Sheets

U.S. PATENT DOCUMENTS

Figure 1:
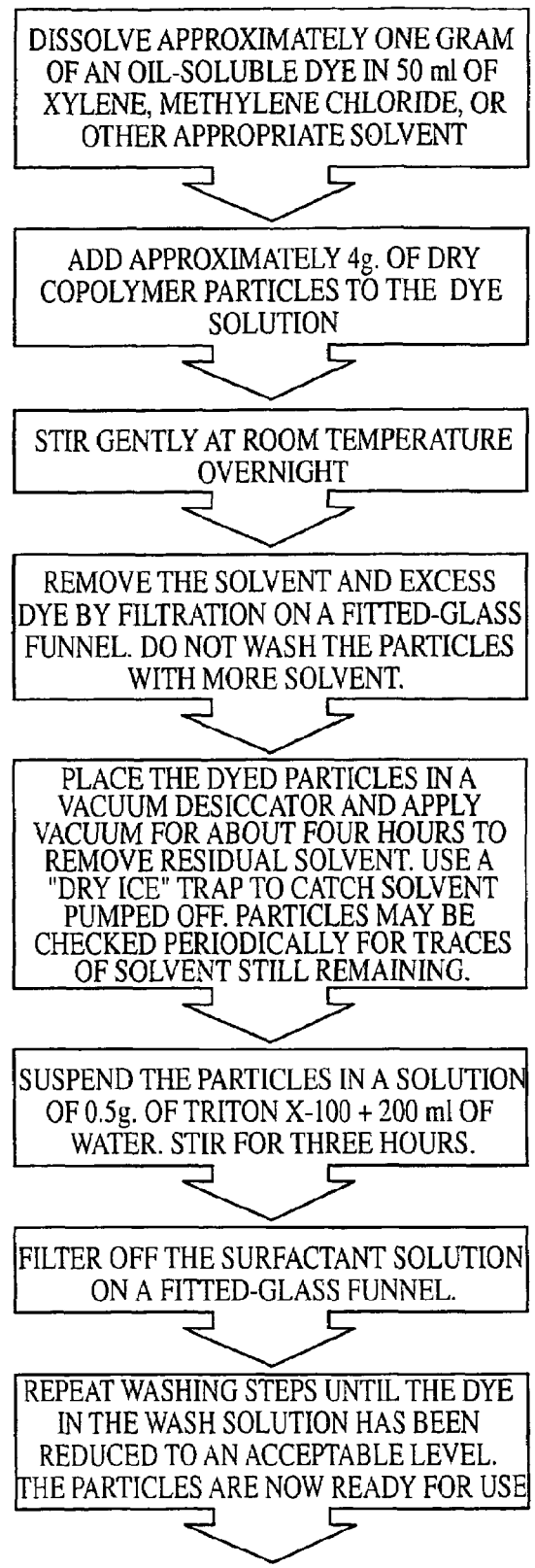

| | | | |
|---|---|---|---|
| 4,267,235 A | | 5/1981 | Rembaum et al. |
| 4,552,812 A | | 11/1985 | Margel et al. |
| 4,677,045 A | | 6/1987 | Champ et al. |
| 4,677,138 A | | 6/1987 | Margel |
| 4,717,655 A | | 1/1988 | Fulwyler |
| 4,774,189 A | | 9/1988 | Schwartz |
| 5,073,498 A | | 12/1991 | Schwartz et al. |
| 5,194,300 A | | 3/1993 | Cheung |
| 5,227,498 A | | 7/1993 | Lee et al. |
| 5,237,498 A | | 8/1993 | Tenma et al. |
| 5,326,692 A | * | 7/1994 | Brinkley et al. ............ 435/6 |
| 5,354,873 A | | 10/1994 | Allen et al. |
| 5,492,795 A | | 2/1996 | Allen et al. |
| 5,573,909 A | * | 11/1996 | Singer et al. ............ 435/6 |
| 5,656,750 A | | 8/1997 | Allen et al. |
| 5,716,855 A | | 2/1998 | Lerner et al. |
| 5,723,218 A | | 3/1998 | Haugland et al. |
| 5,747,349 A | | 5/1998 | van den Engh et al. |
| 5,786,219 A | * | 7/1998 | Zhang et al. ............ 436/523 |
| 5,795,981 A | | 8/1998 | Lee et al. |
| 6,268,222 B1 | * | 7/2001 | Chandler et al. ............ 436/523 |
| 6,309,701 B1 | | 10/2001 | Barbera-Guillem |
| 6,335,440 B1 | | 1/2002 | Lee et al. |
| 6,417,402 B1 | | 7/2002 | Das et al. |
| 6,514,295 B1 | | 2/2003 | Chandler et al. |
| 6,528,165 B2 | | 3/2003 | Chandler |
| 6,599,331 B2 | | 7/2003 | Chandler et al. |
| 6,632,526 B1 | * | 10/2003 | Chandler et al. ............ 428/402 |
| 6,649,414 B1 | * | 11/2003 | Chandler et al. ............ 436/63 |
| 6,929,859 B2 | * | 8/2005 | Chandler et al. ............ 428/403 |
| 6,964,747 B2 | * | 11/2005 | Banerjee et al. ............ 264/4.1 |

FOREIGN PATENT DOCUMENTS

| | | |
|---|---|---|
| EP | 0126450 | 11/1984 |

OTHER PUBLICATIONS

L. B. Bangs, Uniform Latex Particles, Seragen Diagnostics, 1984, p. 40.

Sprenger et al., "Das Cyclobuten-Kation, ein neuartiger Chromophor aus Quadratsäure," Angewandte Chemie, vol. 79, No. 12, 1967, pp. 581-582.

Sprenger et al., "Cyclobutendiylium-Farbstoffe," Angewandte Chemie, vol. 80, No. 14, 1968, pp. 541-546.

Maahs et al., "Syntheses and Derivatives of Squaric Acid," Angewandte Chemie, vol. 5, No. 10, 1966, pp. 888-893.

McHugh, "Flow Microsphere Immunoasay for the Quantitative and Simultaneous Detection of Multiple Soluble Analytes," Methods in Cell Biology, vol. 42, 1994, pp. 575-595.

Colvin et al., "the Covalent Binding of Enzymes and Immunoglobulins to Hydrophilic Microspheres," Microspheres: Medical and Biological Applications, 1988, pp. 1-13.

Cantarero et al., "The Adsorptive Characterisrics of Protein for Polystyrene and their Significance in Solid-Phase Immunoassays," Analytical Biochemistry, vol. 105, 1980, pp. 375-382.

Illum et al., "Attachment of Monoclonal Antibodies to Microspheres," Methods in Enzymology, vol. 112, 1985, pp. 67-84.

Law et al., "Squaraine Chemistry. Synthesis, Characterization, and Optical Properties of a Class of Novel Unsymmetrical Squaraines:[4-Dimethylamino)phenyl](4'-methoxyphenyl)squaraine and Its Derivatives," J. Org. Chem., vol. 57, 1992, pp. 3278-3286.

* cited by examiner

PRECISION FLUORESCENTLY DYED POLYMERIC MICROPARTICLES AND METHODS OF MAKING AND USING SAME

This application is a continuation of application Ser. No. 10/401,549, filed Jul. 3, 2003 now U.S. Pat. No. 6,929,859, which is a continuation of application Ser. No. 09/172,174, filed Oct. 14, 1998, now U.S. Pat. No. 6,632,526, which claims the benefit of provisonal application 60/061,938, filed Oct. 14, 1997 and 60,085,584, filed May 15, 1998.

1. FIELD OF THE INVENTION

The invention generally relates to multicolored, fluorescently stained small particles of generally less than 100 μm in diameter. Disclosed are methods of dyeing or staining such particles or microspheres with at least two fluorescent dyes in such a manner that intra-sample variation of dye concentrations is substantially minimized. Specifically, the invention relates to microspheres stained with at least two fluorescent dyes and methods of using said microspheres for a simultaneous analysis of a plurality of analytes.

2. BACKGROUND OF THE INVENTION

Fluorescent light emitting microparticles, microspheres, microbeads, beads, or particles are now quite common and are useful for a number of practical applications especially in combination with flow cytometry based methods. As used hereinafter the terms: microparticles, microspheres, microbeads, beads, or particles are used interchangeably and bear equivalent meanings. Often, these particles are labeled with just one fluorescent dye. In general, such particles are made by copolymerization process wherein monomers, e.g., unsaturated aldehyde or acrylate, are allowed to polymerize in the presence of a fluorescent dye, e.g., fluorescein isothiocynate (FITC), in the reaction mixture (see for example U.S. Pat. No. 4,267,234 issued to Rembaum; U.S. Pat. No. 4,267,235 Rembaum et al; U.S. Pat. No. 4,552,812, Margel et al.; U.S. Pat. No. 4,677,138, Margel).

One skilled in the art would recognize that two or more dyes of varying proportions could be used to increase the permutation number of unique combinations of dyes in a single particle. These unique characteristics, i.e., emission wavelengths and fluorescence intensities could be extremely useful for multiparameter analysis of a plurality of analytes in the same sample. Three means of making multicolored, fluorescent beads have been reported, including: (a) covalent attachment of dyes onto the surface of the particle, (b) internal incorporation of dyes during particle polymerization, and (c) dyeing after the particle has been already polymerized. All three methods have been disclosed in the prior art.

The examples of the first approach are in U.S. Pat. No. 5,194,300 Cheung; U.S. Pat. No. 4,774,189 Schwartz which disclose fluorescent microspheres that are coated by covalently attaching either one or a plurality of fluorescent dyes to their surface. As such these methods are unrelated to the instant invention dealing with incorporating dyes into particles internally.

Second approach can be found in U.S. Pat. No. 5,073,498 to Schwartz, which discloses two or more fluorescent dyes added during polymerization process and randomly dispersed within the body of the particle. However, when such particles are exposed to a single excitation wavelength only one fluorescent signal is observed at a time and thus these particles are not useful for multiparameter analysis especially in a flow cytometry apparatus with a single excitation light source. The U.S. Pat. No. 4,717,655 issued to Fulwyler discloses two dyes mixed at five different ratios and copolymerized into a particle. Although five populations of beads were claimed as being obtainable the fluorescent properties of these beads were not provided, effectively preventing one skilled in the art to make and use such beads. Thus, Fulwyler method is only a conceptual method since it was not enabled. Furthermore, any of these two methods are unrelated to the instant invention dealing with incorporating fluorescent dyes into already polymerized particles.

The principle of the third method, i.e., internally embedding or diffusing a dye after a particle has been already polymerized was originally described by L. B. Bangs (Uniform Latex Particles; Seragen Diagnostics Inc. 1984, p. 40) and relates to the instant invention as it consists of adding an oil-soluble or hydrophobic dye to stirred microparticles and after incubation washing off the dye. The microspheres used in this method are hydrophobic by nature. This allows adopting the phenomenon of swelling of such particles in a hydrophobic solvent, which may also contain hydrophobic fluorescent dyes. Once swollen, such particles will absorb dyes present in the solvent mixture in a manner reminiscent to water absorption by a sponge. The level and extent of swelling is controlled by incubation time, the quantity of cross-linking agent preventing particle from disintegration, and the nature and amount of solvent(s). By varying these parameters one may diffuse a dye throughout particle or obtain fluorescent dye-containing layers or spherical zones of desired size and shape. Removing the solvent terminates the staining process. Microparticles stained in this manner will not "bleed" the dye in aqueous solutions or in the presence of water-based solvents or surfactants such as anionic, nonionic, cationic, amphoteric, and zwitterionic surfactants.

U.S. Pat. No. 5,723,218 to Haugland et al. discloses diffusely dyeing microparticles with one or more dipyrrometheneboron difluoride dyes by using a process, which is essentially similar to the Bangs method. However, when beads internally stained with two separate dipyrrometheneboron dyes, were excited at 490 nm wavelength, they exhibited overlapping emission spectra, meaning that beads were monochromatic but not multicolored. U.S. Pat. No. 5,326,692 Brinkley et al; U.S. Pat. No. 5,716,855 Lerner et al; and U.S. Pat. No. 5,573,909 Singer et al. disclose fluorescent staining of microparticles with two or more fluorescent dyes. However, dyes used in their process had overlapping excitation and emission spectra allowing energy transfer from the first excited dye to the next dye and through a series of dyes resulting in emission of light from the last dye in the series. This process was intended to create an extended Stokes shift, i.e., a larger gap between excitation and emission spectra, but not the emission of fluorescence from each dye simultaneously. Thus, due to various reasons such as dye-dye interaction, overlapping spectra, non-Gaussian emission profiles and energy transfer between neighboring dyes the demand for multicolored beads simultaneously emitting fluorescence at distinct peaks was not satisfied. Zhang et al. (U.S. Pat. No. 5,786,219) devised microspheres with two-color fluorescent "rings" or microspheres containing a fluorescent spherical "disk" combined with a fluorescent ring. Nevertheless, such beads, designed for calibration purposes, cannot be used in multiparameter analysis since two dyes were mixed only at one fixed ratio. As mentioned above in regard to U.S. Pat. No. 4,717,655 issued to Fulwyler, the highest number of dyes ratios ever attempted with at least two dyes never exceeded five. Thus, until the reduction to practice of the present invention there were no reliable means of creating a series of microsphere populations or subsets in which at least two dyes were mixed at variable, precisely controlled ratios and were proven, upon exposure to a single excitation wavelength, to emit multiple fluorescent signals of variable intensity and at spaced, optically distant wavelengths.

In other words, the prior art failed to provide a reproducible method that would allow one skilled in the art to make a plurality of defined subsets of stained multicolored microparticles distinguishable by a subtle variation in fluorescence signal resulting from the combination of various dyes of distinct color and having variable intensity of color emission. As used hereinafter the term stained microspheres means that a plurality of dyes, which are used to stain a microsphere, are either uniformly diffused throughout the body of said microsphere or penetrated said microsphere in a manner that results in formation of fluorescent rings, disks, and other geometrically distinct patterns.

Clearly, it would be an important improvement to the art to have a means of precisely dyeing or staining a particle with two or more dyes premixed in a series of predetermined ratios and to have a collection of such dyed microspheres for use in multiparameter applications. This precision in dyeing process is commonly expressed as the coefficient of variation, which is the ratio of the standard deviation to the mean intensity of the fluorescent particle population. By minimizing this value, more subsets or populations of non-overlapping, distinctly dyed particles can be obtained. It would be a further advance in the art if the methods were repeatable or reproducible to within a minimal variation, preferably no more than about a 20% intra-sample variation, more preferably no more than about a 15% variation, and most preferably no more than about a 8% variation.

3. SUMMARY OF THE INVENTION

An improved method is described for incorporating two or more fluorescent dyes into already polymerized microspheres. The amount of each dye absorbed by the microsphere is precisely controlled so as to give rise to two or more reproducible fluorescent signals of precise intensities and emission peaks within a given population of particles. A series of such populations or subsets of beads are dyed in batches each one of them having predetermined ratio or proportion of two or more fluorescent dyes. Due to novel and improved method of staining, the particle-to-particle variation in the same batch is greatly reduced, which allows producing an unprecedented number of distinct populations of multicolored, fluorescent microspheres residing within optically uniform, tightly defined cluster.

Accordingly, a set containing optically distinct precision stained microspheres is also claimed which would be useful for simultaneous analysis of a plurality of analytes in a same sample. In other words, said beads will provide a lot more than the use of stained beads found in the prior art since the number of analytes that can be measured simultaneously in a single tube, using a single sample aliquot is drastically increased. The fluorescent microparticle obtained by the inventive staining method is characterized by having at least two fluorescent dyes mixed within the body of the particle and each one of them capable of giving off, simultaneously, multiple fluorescent emission lights of predetermined color and intensity. The combination of notions relating to the emission peak corresponding to a given color and intensity of the fluorescent color as expressed in fluorescence channel units is generally termed as the fluorescence signal. The specific ratio or proportion of dyes at which they are mixed within a population of particles will determine the location of said populations on a fluorescence map, which allocates these populations according to fluorescent color and brightness. By using as little as two dyes, e.g., orange and red, as many as 64 populations of beads are made each one distinct from another by subtle variations in unique fluorescence characteristics recognized by a flow cytometry apparatus.

When each such population of beads, characterized by at least two fluorescent signals, is combined with an analytical reactant capable of binding a specific analyte in a clinical or test sample a powerful analytical tool is obtained, which can provide qualitative and quantitative assay results. The analytical method is also provided which is based on using multicolored fluorescent beads obtained by the instant invention. To achieve truly multiplexed analysis of a plurality of analytes in a sample, a third type of fluorescent signal, e.g., green fluorescent signal is provided, usually found in a label reagent, which is capable of binding the analyte of interest. Thus, methods of making multicolored beads, the beads themselves, multiple sets of such beads, and multiplexed methods of analyzing a plurality of analytes in a single sample are claimed by the instant invention.

A method of staining polymeric microspheres with two or more fluorescent dyes is disclosed, which method comprises: (a) combining at least two fluorescent dyes in a solvent mixture comprising at least one organic solvent in which the at least two fluorescent dyes are soluble and at least one alcoholic solvent in which the at least two fluorescent dyes are less soluble, to provide a solution of mixed dyes which is further characterized as having the capacity to swell at least partially but not dissolve a plurality of polymeric microspheres, which is brought into contact with the solution; (b) contacting a plurality of polymeric microspheres with the solution for a period of time sufficient to provide uniform staining of substantially all of the members of the plurality of polymeric microspheres with the at least two fluorescent dyes, the at least two fluorescent dyes being selected such that on isolation and excitation of the dyed plurality of polymeric microspheres, a distinct fluorescence signal is emitted from each dye, the intensity of which emitted signal is proportional to the amount of the dye in the dyed plurality of polymeric microspheres.

In a particular embodiment of the invention, the method further comprises dehydrating the plurality of polymeric microspheres. Such a dehydrating step is accomplished by washing the plurality of polymeric microspheres one or more times with an alcoholic solvent prior to contacting the microspheres with the solution of mixed dyes. In still a preferred method, the dehydrating step involves drying the washed microspheres or allowing the alcoholic solvent to evaporate from the washed microspheres prior to contacting the microspheres with the solution of mixed dyes.

Typically, the dyed plurality of polymeric microspheres is isolated by any manner well known in the art, including but not limited to filtration or centrifugation. It has been found desirable to obtain dyed plurality of polymeric microspheres in which at least one of the fluorescent dyes is diffused throughout the interior of substantially all of the members of the dyed plurality of polymeric microspheres, or in which the at least two fluorescent dyes are diffused throughout the interior of substantially all of the members of the dyed plurality of polymeric microspheres. Still other advantages can be gained by providing dyed plurality of polymeric microspheres in which at least one of the fluorescent dyes is diffused through only a portion of the interior of substantially all of the members of the dyed plurality of polymeric microspheres.

In a specific method of the invention, the staining procedure further comprises preparing a series of the solutions having differing desired ratios of the at least two fluorescent dyes and further comprises contacting separate populations of a plurality of polymeric microspheres with the series of the solutions to provide multiple distinct populations or subsets of a plurality of polymeric microspheres, each distinct population or subset having a differing desired ratio of the at least two fluorescent dyes.

It has been observed that the distinct fluorescence signals emitted from the at least two fluorescent dyes differ in their respective wavelengths by at least about 10 nm, preferably by at least about 30 nm and most preferably by at least about 50 nm.

Hence, the present invention provides a population of polymeric microspheres substantially uniformly stained with at least two fluorescent dyes, each microsphere of the population upon excitation exhibiting at least two distinct fluorescence emission signals corresponding to the at least two fluorescent dyes, the intensity of each of the at least two emitted signals (i) being proportional to the amount of its corresponding dye in the microsphere, and (ii) exhibiting a coefficient of variation among all the members of the population, which is no greater than about 20 percent. In particular, preferred populations are those in which the intensity of each of the at least two emitted signals exhibits a coefficient of variation among all the members of the population, which is no greater than about 15 percent, more preferably no greater than about 10 percent and most preferably no greater than about 8 percent. In still other embodiments, the intensity of each of the at least two emitted signals exhibits a coefficient of variation among all the members of the population, which is less than about 8 percent.

The present invention offers, thus, a collection of distinct populations of polymeric microspheres according to the specifications described above, each population exhibiting an emission spectrum in a Fluorescence Bead Map, which is unique to the population. In specific embodiments, the collection comprises eight or more distinct populations of polymeric microspheres, preferably sixteen or more distinct populations of polymeric microspheres, more preferably twenty-four or more distinct populations of polymeric microspheres, most preferably thirty-two or more distinct populations of polymeric microspheres and still most preferably sixty-four or more distinct populations of polymeric microspheres. Generally, the collection is further characterized in that there is substantially no overlap between any of the sixty-four or more emission spectra associated with the sixty-four or more distinct populations of polymeric microspheres.

Also contemplated by the invention, is a method of detecting simultaneously by flow cytometry a plurality of analytes in a sample, each of the analytes being recognized by a corresponding analytical reactant, comprising: (a) contacting the sample with a plurality of populations of uniformly stained microspheres, the microspheres having at least two fluorescent dyes uniformly mixed at a specific ratio within each microsphere of each the population, each population of the microspheres having a distinct analytical reactant bound to its surface, wherein, the reactant on each population of microspheres specifically interacts with one of the analytes in the sample; (b) providing a label reagent that specifically binds to the analyte and analyzing the microspheres to detect the label indicating binding of the analyte to the analytical reactant; and (c) determining the populations of microspheres having the fluorescent dyes mixed at the specific ratio within microspheres of each population to which the reactant is bound.

Other objects of the invention will become apparent from the further discussions and detailed descriptions provided herein.

OVERVIEW OF THE INVENTION AND ITS EMBODIMENTS

Recent developments in instrumentation have necessitated the concurrent development of multiple and precisely dyed microspheres that can emit multiple fluorescent signals simultaneously. This invention describes techniques for absorbing at least two squaric acid-based fluorescent dyes into polymeric, i.e., polystyrene particles.

The present invention describes techniques for precisely dyeing polystyrene microspheres of sizes ranging from approximately 10 nm to 100 μm in diameter. The size of particles is immaterial to this invention since the precision of the dyeing process is not affected. The only requirement is that particles are made of water-insoluble material but soluble in adequate solvents. The dyes employed are preferably squaric acid-based molecules that exhibit fluorescence extending into near infrared and/or infrared region, i.e., to ca. 1,000 nm. Use of other dyes may allow one to expand the range from the ultraviolet to infrared. This method allows for a highly reproducible process in which two or more dyes of independent concentration are absorbed uniformly into each microsphere, resulting in multiple fluorescent signals respective of the number of dyes present in the microsphere.

The technology is disclosed enabling one skilled in the art to make a series of multicolored, fluorescent particles with unique fluorescence characteristics and using such particles for multiparameter analysis of a plurality of analytes simultaneously.

4. BRIEF DESCRIPTION OF DRAWINGS

FIG. 1 showing flow chart with sequential steps of dyeing polymeric particles using the prior art technique.

Figure 2:
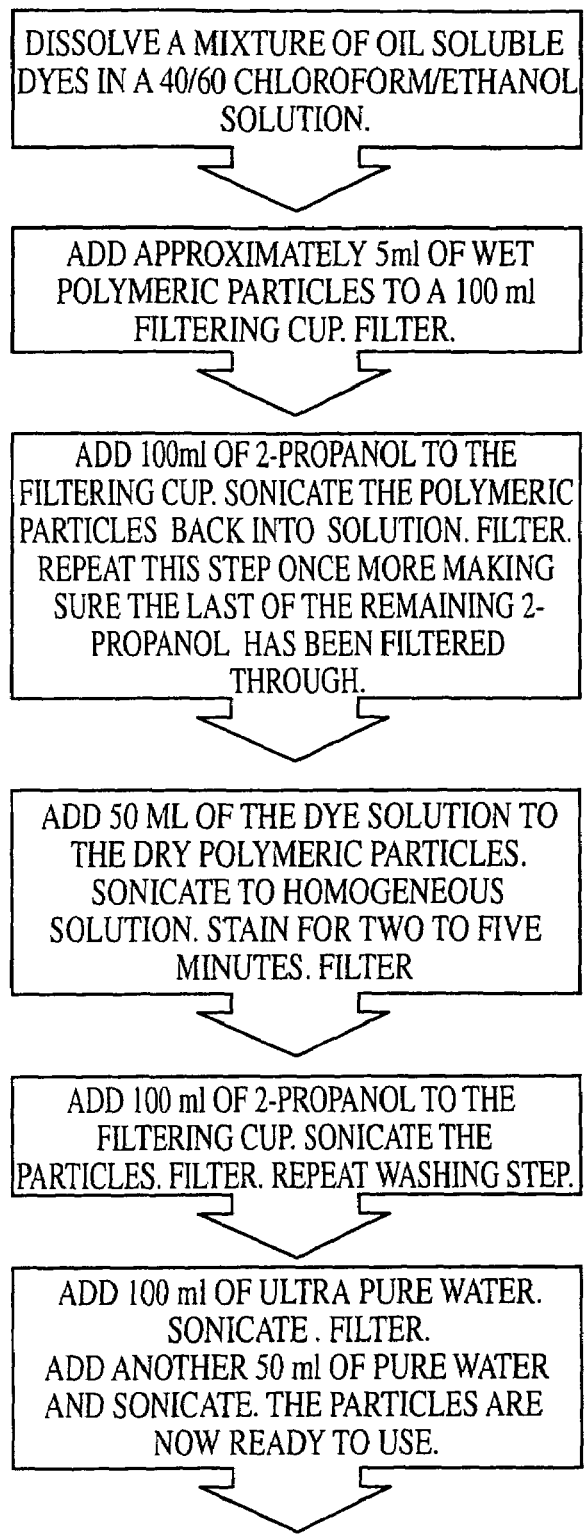

FIG. 2 showing flow chart with sequential steps of dyeing polymeric particles using the instant invention.

Figure 3:
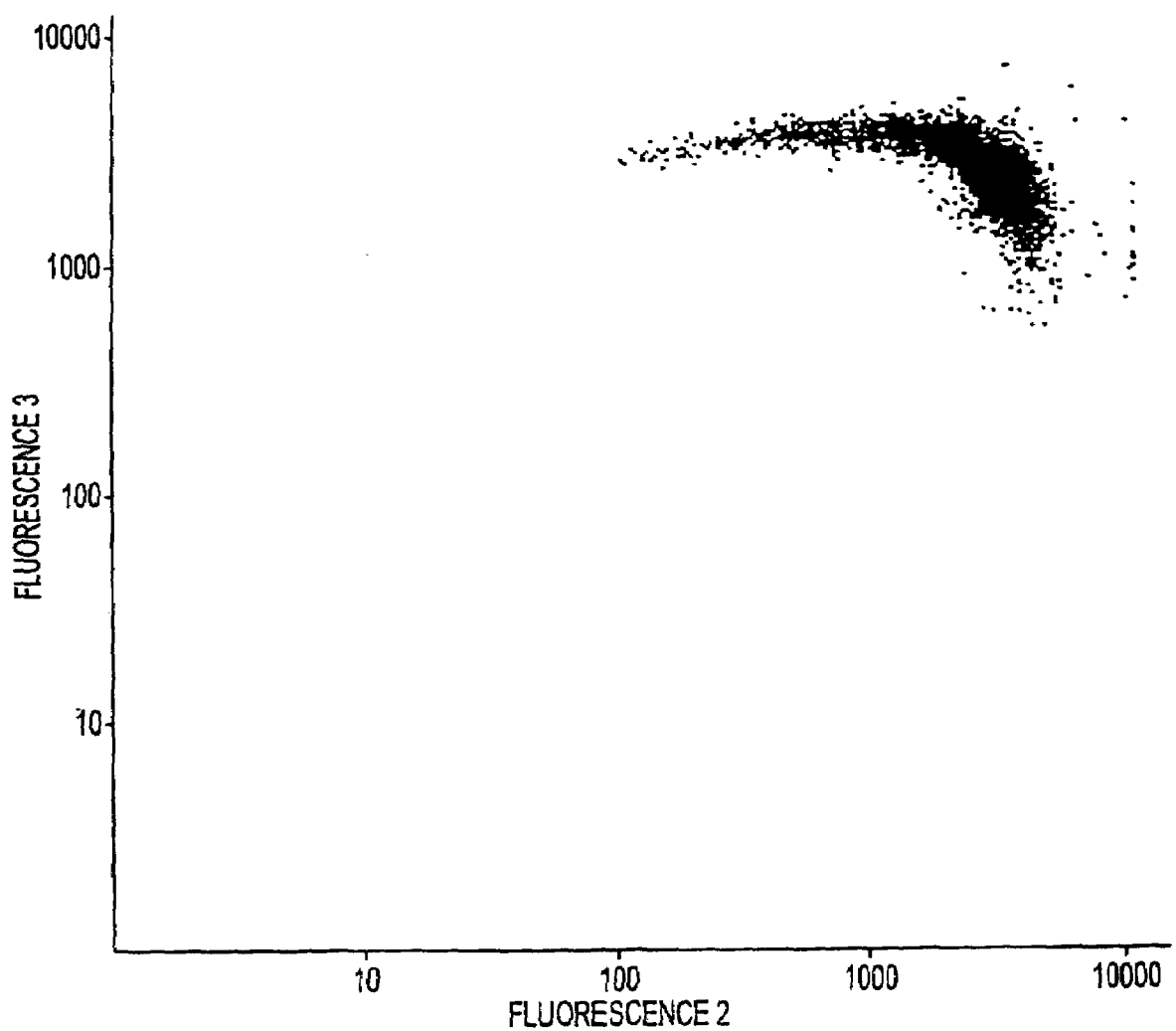

FIG. 3 showing two-dimensional flow cytometry chart illustrating wide optical distribution of two-color-dyed microspheres using the prior art technique.

Figure 4:
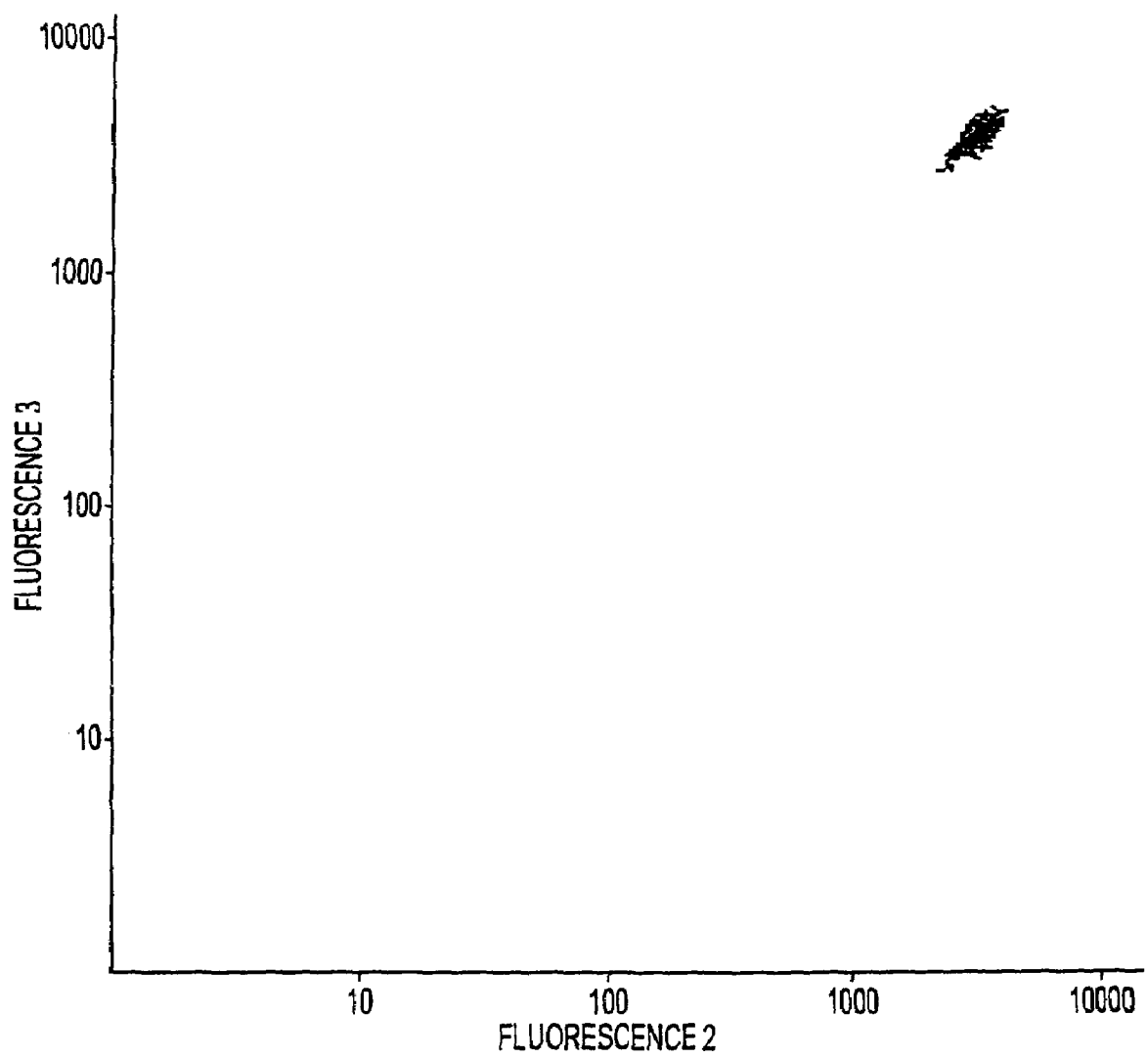

FIG. 4 showing two-dimensional flow cytometry chart illustrating tight clustering of two-color-dyed microspheres using the instant invention.

Figure 5:
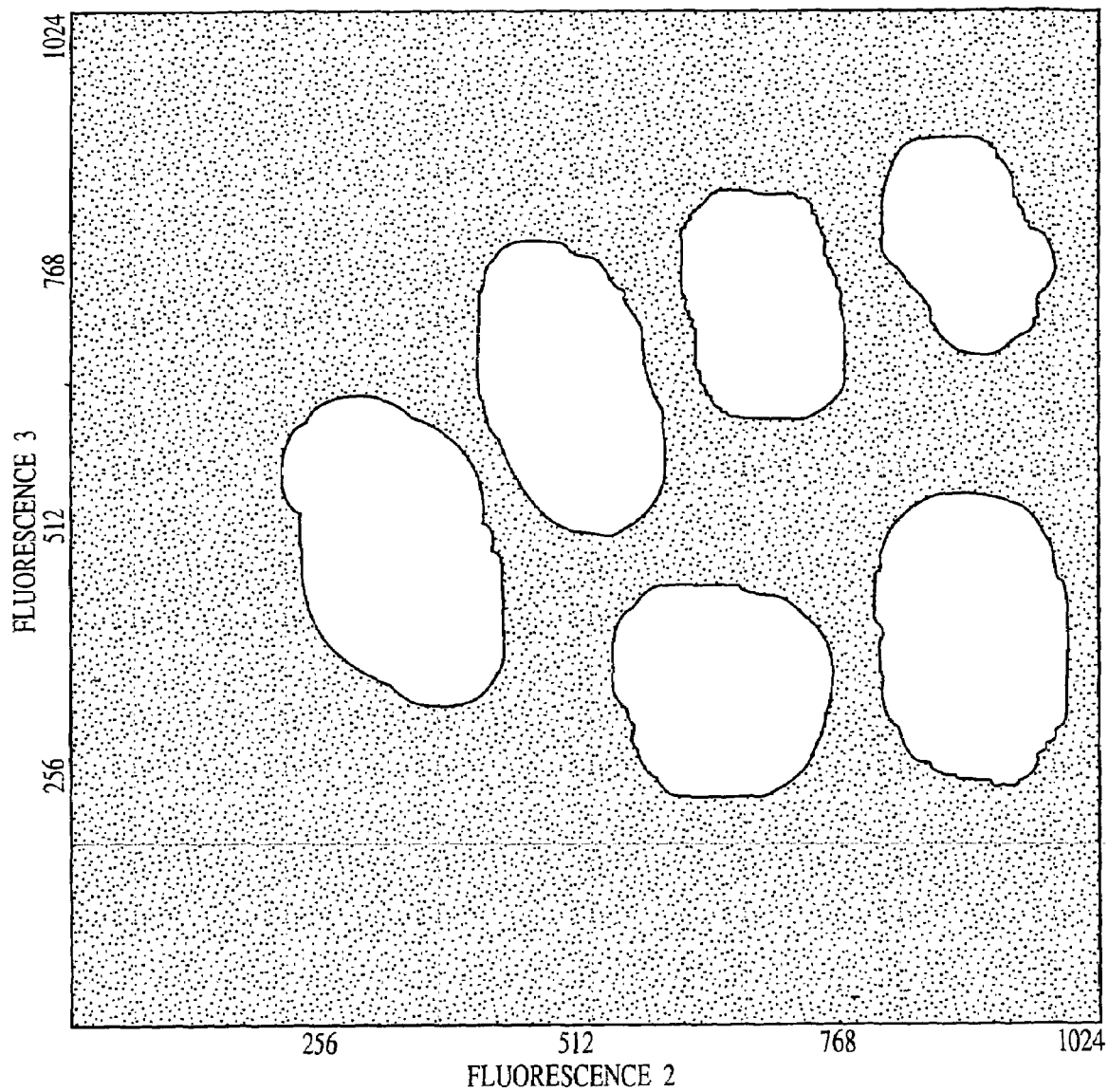

FIG. 5 showing that prior art method allows no more than 6 subsets of multicolored bead populations on a Fluorescence Bead Map.

Figure 6:
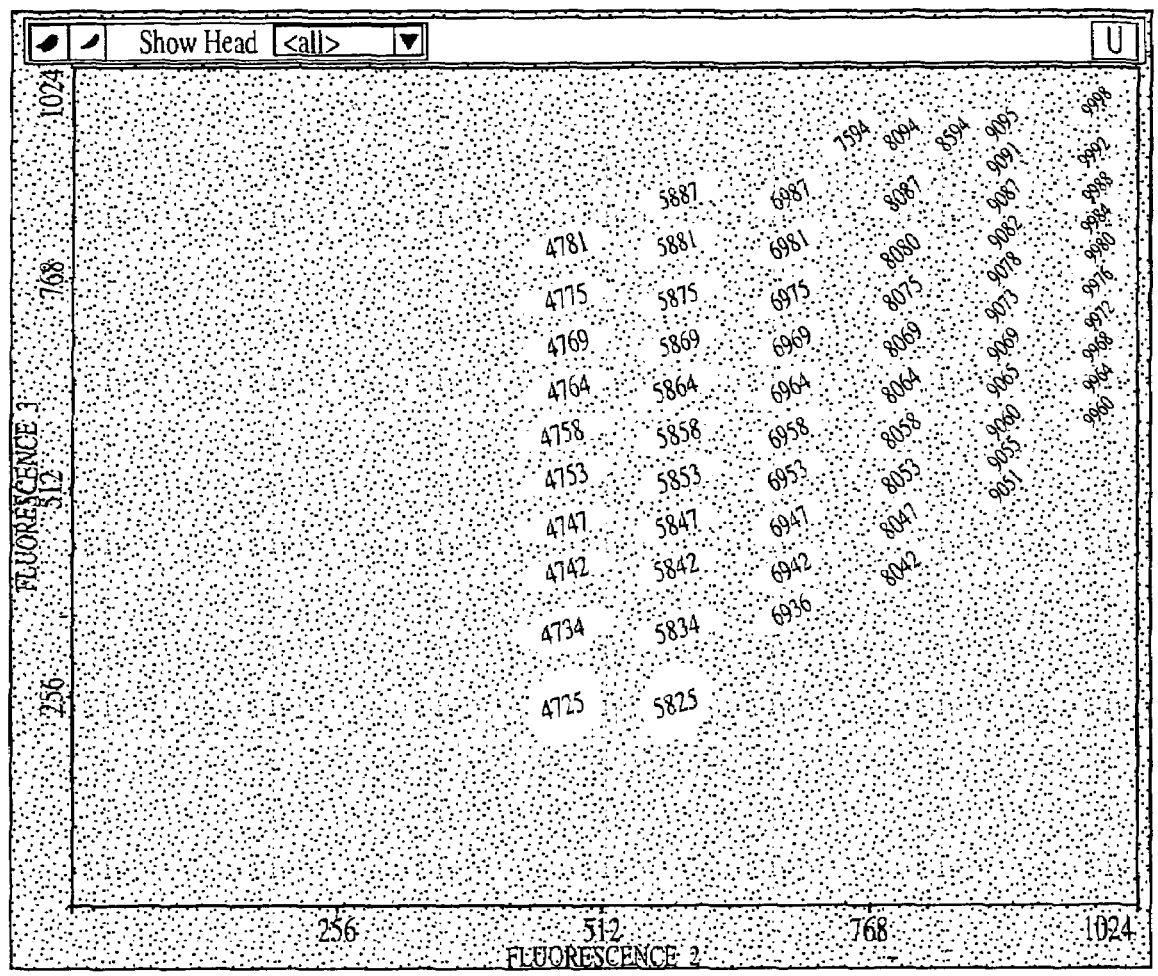

FIG. 6 showing Fluorescence Bead Map for 64-Region Bead Set, indicating tight distribution of each bead subset fluorescence characteristics within boundaries prescribed by each region.

5. DETAILED DESCRIPTION OF SPECIFIC EMBODIMENTS

The invention provides novel polymeric beads or microspheres containing at least two fluorescent dyes. This invention further includes the improved method of making such beads by mixing said beads with at least two fluorescent dyes combined at predetermined ratio so that optically distinct, multiple populations of multicolored beads are formed. These bead populations are easily discriminated as essentially non-overlapping clusters by visual detection methods such as microscopy or preferably by flow cytometry. The method of simultaneous, multiparameter analysis of a plurality of analytes is also provided whereby each distinct multicolored bead population would carry an additional analytical reactant, e.g., antibody, antigen, or nucleic acid probe, which would react with a specific analyte of interest in a sample containing the plurality of analytes.

Polymeric microspheres used in this invention are commercially available from a number of vendors and range in size from 0.01 to 100 micrometers (μm) in diameter. Even though the microparticle can be of any size, the preferred size is 0.1-50 μm, more preferably 1-20 μm, and even more preferably 3-9 μm. The sizes of beads in one set can be uniform or may differ in order to distinguish and classify them into further subsets according to their size. The size of the microparticle can be measured in practically any flow cytometry apparatus by so-called forward or small-angle scatter light. These subsets can be also further distinguished by different shape of microparticles. The shape of the particle can be also discriminated by flow cytometry, e.g., by high-resolution slit-scanning method.

The preferred make of microspheres is polystyrene or latex material. However, any type of polymeric make of microspheres is acceptable including but not limited to brominated polystyrene, polyacrylic acid, polyacrylonitrile, polyacrylamide, polyacrolein, polybutadiene, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, or combinations thereof.

The microspheres will also contain 1 to 30% of a cross-linking agent, such as divinyl benzene, ethylene glycol dimethacrylate, trimethylol propane trimethacrylate, or N,N'methylene-bis-acrylamide or other functionally equivalent agents known in the art. In preferred embodiment microspheres are made of polystyrene and contain 1 to 30% divinyl benzene.

The beads may or may not have additional surface functional groups, such as carboxylates, esters, alcohols, carbamides, aldehydes, amines, sulfur oxides, nitrogen oxides, or halides. The functionality of the microspheres' surface groups gives the microspheres their coupling capability allowing chemical binding of analytical reactants. In addition to functional groups on microspheres the dyes themselves can also carry chemically reactive functional groups which in addition to groups listed above can also be carboxylic acid, carboxylic acid succinimidyl ester, carboxylic acid anhydride, sulfonyl chloride, sulfonyl fluoride, hydrazine derivatives, acyl azide, isocyanate, haloacetamide, phenols, thiols, and ketones. These functional groups are useful for attachment of analytical reactants, i.e., classical, commonly used reactants such as antibody, antigen (hapten), digoxigenin, or nucleic acid probe. These may also include reactants that can form specific, high-affinity conjugates such as avidin-biotin, receptor-ligand, ligand-ligate, enzyme-substrate, lectin-carbohydrate, protein A-immunoglobulin, etc. For flow cytometry analysis the analytical reactants are commonly labeled with fluorescent tags or labels such fluorescein (FITC) or rhodamine. These light-emitting conjugates of a dye and analytical reactant are termed as label reagents.

The analytical reactants can be also selected among fluorescent reporter molecules capable to react with a variety of analytes, e.g., $O_2$, $CO_2$, pH, $Ca^{++}$, $Na^+$, $K^+$, or $Cl^-$ as disclosed for example in U.S. Pat. No. 5,747,349 issued to van den Engh et al.

Suitable solvents will be selected based on their ability to solubilize the particular class of hydrophobic dyes of interest. It is preferable that their solubility characteristics are substantially similar. The solvents can be acyl, aliphatic, cycloaliphatic, aromatic or heterocyclic hydrocarbons; the solvents may or may not have halogens, oxygen, sulfur, nitrogen, and/or phosphorous as either terminal groups or as integral parts of a ring or chain. Specifically, solvents such as toluene, xylene, hexane, pentane, acetone, DMSO, or methylene chloride can be used. In a preferred embodiment, chlorinated solvents, more preferably chloroform, are used to solubilize the squaric acid class of dyes, which are preferred dyes used in this invention.

In one embodiment two fluorescent squaraine dyes are used, e.g., red dye which is 1,3-bis[(1,3-dihydro-1,3,3-trimethyl-2H-indol-2-ylidene)methyl]-2,4-dihydroxy-cyclobutenediylium, bis(inner salt) and orange dye is 2-(3,5-dimethylpyrrol-2-yl)-4-(3,5-dimethyl-2H-pyrrol-2-ylidene)-3-hydroxy-2-cyclobuten-1-one. The molar ratio between first and second dye, when present in a bead, will preferably be between about 0 and 10,000, more preferably between 0.00001 and 2,000. Both dyes would preferably be excited at the same absorption wavelength, e.g., ranging from ultraviolet to about 800 nm, and emit fluorescent light at two distinct, essentially non-overlapping wavelengths distant from each other by at least 10 nm, preferably 30 nm, and more preferably by at least 50 nm. For example, the emission peak of the dye #1 is at 585 nm, and the peak emission of dye #2 is at 630 nm.

The squaric acid based fluorescent dyes can be synthesized by methods described in the literature. See, for example, Sprenger et al. Angew. Chem., 79, 581 (1967); Angew. Chem. 80, 541 (1968); and Maaks et al., Angew Chem. Intern. Edit. 5, 888 (1966). Briefly, one equivalent of squaric acid (1,2-dihydroxycyclobutenedione) is condensed with two equivalents of an active compound, such as a pyrrole, indoline, or aniline, and refluxed in a mixture of an alcohol and an aromatic solvent (such as benzene) under conditions that allow removal of water from the reaction mixture. The resulting dye can be collected and purified by a number of standard methods, such as recrystallization, distillation, chromatography, etc. Additionally, unsymmetrically substituted squaric acid compounds can be synthesized by methods such as those described by Law et al., J. Org. Chem. 57, 3278, (1992). Specific methods of making some of such dyes are well known in the art and can be found for example in U.S. Pat. Nos. 5,795,981; 5,656,750; 5,492,795; 4,677,045; 5,237,498; and 5,354,873. Optionally such dyes will contain functional groups capable of forming a stable fluorescent product with functional groups typically found in biomolecules or polymers including activated esters, isothiocyanates, amines, hydrazines, halides, acids, azides, maleimides, alcohols, acrylamides, haloacetamides, phenols, thiols, acids, aldehydes and ketones.

In addition to specific squaric acid dyes are used in this preferred embodiment, related dyes can be further selected from cyclobutenedione derivatives, substituted cephalosporin compounds, fluorinated squaraine compositions, symmetrical and unsymmetrical squaraines, alkylalkoxy squaraines, or squarylium compounds. Some of these dyes can fluoresce at near infrared as well as at infrared wavelengths that would effectively expand the range of emission spectra up to about 1,000 nm.

In addition to squaraines, i.e., derived from squaric acid, hydrophobic dyes such as phthalocyanines and naphthalocyanines can be also selected as operating at longer wavelengths. Other classes of fluorochromes are equally suitable for use as dyes according to the present invention. Some of these dyes are listed herein: 3-Hydroxypyrene 5,8,10-Tri Sulfonic acid, 5-Hydroxy Tryptamine, 5-Hydroxy Tryptamine (5-HT), Acid Fuhsin, Acridine Orange, Acridine Red, Acridine Yellow, Acriflavin, AFA (Acriflavin Feulgen SITSA), Alizarin Complexon, Alizarin Red, Allophycocyanin, ACMA, Aminoactinomycin D, Aminocoumarin, Anthroyl Stearate, Aryl- or Heteroaryl-substituted Polyolefin, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, BOBO 1, Blancophor FFG Solution, Blancophor SV, Bodipy Fl, BOPRO 1,Brilliant Sulphoflavin FF, Calcien Blue, Calcium Green, Calcofluor RW Solution, Calcofluor White, Calcophor White ABT Solution, Calcophor White Standard Solution, Carbocyanine, Carbostyryl, Cascade Blue, Cascade Yellow, Catecholamine, Chinacrine, Coriphosphine O, Coumarin, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, DAPI, Diamino Phenyl Oxydiazole (DAO), Dimethylamino-5-Sulphonic acid, Dipyrromethenboron Difluoride, Diphenyl Brilliant Flavine 7GFF, Dopamine, Eosin, Erythrosin ITC, Ethidium Bromide, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Hoechst 33258 (bound to DNA), Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nile Red, Nitrobenzoxadidole, Noradrenaline, Nuclear Fast Red, Nuclear Yellow, Nylosan Brilliant Flavin E8G, Oregon Green, Oxazine, Oxazole, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Propidium Iodide, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Rose Bengal, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulphO Rhodamine B Can C, Sulpho Rhodamine G Extra, Tetracycline, Texas Red, Thiazine Red R, Thioflavin S, Thioflavin TCN, Thioflavin 5, Thiolyte, Thiozol Orange, Tinopol CBS, TOTO 1, TOTO 3, True Blue, Ultralite, Uranine B, Uvitex SFC, Xylene Orange, XRITC, YO PRO 1, or combinations thereof. One skilled in the art would certainly know which one to select among such dyes as long as desired emission and absorption properties as well as their hydrophobic properties are appropriate. The spectral properties of the fluorescent dyes should be sufficiently similar in excitation wavelengths and intensity to fluorescein or rhodamine derivatives as to permit the use of the same flow cytometry equipment. It is preferable that the dyes, however, have higher solubility in organic solvents and have improved photostability and quantum yields. These dyes will be combined at predetermined ratio and embedded into a microsphere vehicle and total dye quantity will be between about 0.00001% and 15% by weight to particle weight. This limitation is however of little consequence to the present invention for as long as the particle impregnated with said dyes is stable and usable for its intended purpose.

Prior Art Method.

The prior art method teaches staining carrier particles with a single dye only (see FIG. 1). However, for the purpose of a meaningful comparison and in order to be consistent with the thrust of the instant invention, the said method was adapted to stain with two dyes simultaneously. The prior art of dyeing large polymer particles (>5 um) as stated in "Uniform Latex Particles" by Leigh B. Bangs was performed and the general outline of the procedure is shown in FIG. 1 and obtained results are shown in FIG. 3. Briefly, the process is started by placing 5 ml of undyed stock microspheres in an aqueous medium directly on a membrane covered fritted funnel. A vacuum pump pulled air through the microspheres plated onto the filter paper for one hour. Next, the dried microspheres were transferred to 50 ml of dye solution, covered, and stirred at room temperature over night. The next day the microspheres were separated by filtration from the dye solution and the dyed particles were placed in a vacuum dessicator for about four hours to remove residual solvent. Next is added 200 ml of Triton X-100 and water solution to the dried dyed microspheres in a 250 ml flask. The solution is stirred for three hours. The solution is filtered and the washing is repeated until no further dye is detected in the filtrate. The beads stained in this manner are tested for staining uniformity by flow cytometry (FIG. 3). It can be easily seen that, based on three separate experiments (tests A, B, and C), bead-to-bead variation at FL2 and FL3 parameters (CV or coefficient of variation) is rather high and inadequate (Table 1) to satisfy the increasing demand for precisely dyed multicolored microspheres.

General Outline of the Instant Method.

As the demand and applications for precisely dyed multicolored microspheres increases the development of alternate processes to the aforementioned method is warranted. As a result, a modification of the prior art method has been developed which has proven to be the most efficient method for precision dyeing of the microspheres (see FIG. 2). This method takes one tenth or even less of the time of the previously mentioned method and significantly enhances its precision. As before, it is critical to remove almost all traces of water from the microspheres. To accomplish this a volume of stock microspheres in an aqueous medium is pipetted onto a vacuum filter membrane, and the liquid is removed and discarded. Next, 100 ml of the rinse solvent (an aliphatic alcohol, such as propanol, methanol, ethanol, etc.) are added to the microspheres. The microspheres are resuspended by placing an ultrasonic probe directly into the solution and applying power for several seconds or as needed to affect resuspension. The suspension is filtered and previous step is repeated once more. Dyeing of the microspheres is accomplished by adding 50 ml of a dye solution (composed of one or more dyes in an organic solvent, as described below) to the filtering cup and resuspending as before. The suspension is allowed to sit for five minutes in the filtering cup. Next, 50 ml of rinse solvent is added to the dye suspension, sonicated and filtered. Another 100 ml of the rinse solvent is added, resuspended and filtered. The last step is repeated once more. In order to prepare the microspheres for storage, 100 ml of an aqueous medium is added to the microspheres, then sonicated and filtered. Finally, 50 ml of aqueous medium is added to the microspheres, sonicated and transferred to a storage container.

In a particular embodiment of the invention, two squaric acid-based dyes are mixed in a solvent suitable for the complete dissolution of both dyes, such as chloroform. Ethanol is added to the solution to increase wetting of the microspheres, and to create a process-dependent, final solvent density that is less than that of the microspheres. The concentrations of each dye are experimentally determined as a function of the target fluorescence intensity at each of the two center wavelengths. These concentrations maintain their relative intensity throughout this inventive process.

An important aspect of the present invention is the preparation of microspheres prior to the dyeing operation. Manufacturers often supply microspheres in an aqueous medium. It has been discovered that the surface of the microsphere that had been stored in aqueous medium must be treated to make it permeable to organic compounds. In a preferred embodiment, an amount of a polar organic solvent such as an alcohol is added to the microsphere solution to achieve about a 50% mixture of the aqueous medium and the polar organic solvent. This ratio, however, may vary and adjusted at will according to particular needs that one may have or determined by chemical and physical properties of medium and solvent.

An equally efficient and precise technique involves "drying" the microspheres through a series of alcohol, e.g., methanol, ethanol, 2-propanol, rinses. The process begins by spinning down the aqueous suspension of microspheres, typically 10% solids in suspension. The aqueous medium is decanted, and the beads are re-suspended in methanol. The alcohol solution at ca. 5% solids is vortexed, sonicated and spun down. This step is performed once or twice more. The excess alcohol is decanted from the pellet, and residual solvent is evaporated under vacuum.

Test samples consisting of 0.05 gram of dried microspheres are used to help adjust the dye solution to its desired ratio. The dried 0.05 gram of microspheres are suspended in 0.5 ml of dye mixture containing two or more dyes of interest. The suspension of microspheres, now at 10% solids, is vortexed and sonicated into suspension. Once in suspension the mixture of microspheres and dyes is mixed for one hour. After that hour, the microspheres are spun down for a period of 1 minute using a centrifuge. The dye solution is decanted back into the main flask, and the 0.05 g of microspheres are re-suspended in 1 ml of 90% of alcohol, e.g., methanol. The rinse step uses double the volume of the dye solution, thus maintaining a 5% solid solution. The sample is vortexed, sonicated and spun down. The methanol supernatant is decanted. The 90% methanol rinse step is repeated once more. Finally, the excess methanol is decanted from the pellet, and the microspheres are re-suspended in an aqueous medium. The resulting test samples are then tested to determine the fluorescence activity/intensity of the labeled beads.

When the test samples show that the dye solution, indeed, has the precise ratios of the desired dyes, a macro-scale batch is conducted. The principle of macro-scale work up is identical to that noted above. Briefly, 25 ml of the desired dye solution is transferred to a 50 ml vial, which contains 2.5 grams of dried microspheres. The microspheres, now at 10% solids, are vortexed and sonicated. Once the microspheres are completely in suspension, it is mixed for an hour. After that hour the microspheres are taken out of the dye solution by centrifugation. The dye solution is decanted back into the main flask, and the 2.5 grams of microspheres are re-suspended in 50 ml of 90% methanol. The rinse step uses double the volume of the dye solution, thus maintaining a mixture of 5% solids. The sample is vortexed, sonicated and spun down. The methanol supernatant is decanted. This step is repeated once more. After the final methanol rinse is decanted, the microspheres are put through an aqueous rinse. The aqueous supernatant is decanted, and the beads are then re-suspended and stored in a fresh aqueous medium.

The following Examples are presented to illustrate the advantages of the present invention and to assist one of ordinary skill in making and using the same. These Examples are not intended in any way to otherwise limit the scope of the disclosure or the protection granted by Letters Patent hereon.

EXAMPLE 1

A single solution containing two different squaric acid dyes is prepared. One dye is a red fluorescent dye 1,3-bis[(1, 3-dihydro-1,3,3-trimethyl-2H-indol-2-ylidene)methyl]-2,4-dihydroxy-cyclobutenediylium, bis(inner salt) and second dye is orange fluorescent dye can be 2-(3,5-dimethylpyrrol-2-yl)-4-(3,5-dimethyl-2H-pyrrol-2-ylidene)-3-hydroxy-2-cyclobuten-1-one. The peak emission of dye #1 is 585 nm, and the peak emission of dye #2 is 630 nm. These dyes are chosen because they fall in the center of two of the fluorescence channels of a Becton Dickinson FACScan flow cytometer, which is the measurement device used to determine the precision of prior art dyeing techniques compared with this innovative new technique. The choice of fluorescence channels is, however, relative and immaterial since another flow cytometry apparatus may have different settings.

Two samples of undyed microspheres are prepared. The first is dyed with the mixture of orange and red dyes using this innovative technique (shown FIGS. 2 and 4), and the second is dyed using the prior art technique (FIGS. 1 and 3). Samples are measured on the FACScan, and an X-Y plot is generated to show the relative homogeneity of each sample. X-axis represents brightness or fluorescence intensity of orange dye and Y-axis represents the same parameters of red dye. Mean intensities and coefficients of variation are also measured. It is clear that beads stained by the old method spread over much larger X-Y area, indicating that the ratio of orange and red dyes vary from particle-to-particle. In contrast, the coefficient of variation in the bead population dyed by the instant, improved method is much smaller. About 10,000 beads in each tests A, B, and C, were run in parallel with beads stained by Bangs method (Table 1).

EXAMPLE 2

To make another population of beads with different fluorescent characteristics the ratio of red/orange dyes is altered by an adequate increment in proportion of dyes so that obtained population optically does not overlap with the former population. The prior art failed to provide multiple populations of multicolored beads due to inevitable intra-sample heterogeneity resulting from inadequate staining process resulting in poor dye distribution from particle-to-particle within given staining batch. Thus, upon excitation with a light source, stained beads containing more than one dye failed to emit uniform fluorescence signals of desired intensity. The instant invention overcomes this problem and achieves construction of as many as 64 subsets of optically distinct beads by varying the ratio of just 2 dyes. This example is not in any way a limiting one since one of ordinary skill may easily generate smaller or higher number of bead subsets by using the instant teaching. One skilled in the art may appreciate that nothing even close to this achievement has ever been enabled in the actual practice. Although such an eventuality was theoretically speculated as a possible one, the prior art failed to teach one of ordinary skill how to arrive at that.

The present inventors were able, for the first time, to reduce to practice the invention and representative experimental results of obtaining 64-bead population are shown in FIG. 6 and Table 2. The results illustrated in FIG. 5 show multicolored beads by using staining procedure of the prior art method. Due to imprecision in staining technique, which results in a wide dispersion of dyes ratio from bead-to-bead, no more than 6 subsets of multicolored bead populations can be fitted on a Fluorescence Bead Map. In contrast, FIG. 6 shows Fluorescence Bead Map containing 64 populations of beads, indicating tight distribution of each bead subset fluorescence characteristics within boundaries prescribed by each region. The cross-talk between various clusters is minimal. Most of the overlap is due to the presence of bead agglomerations which emit brighter signal but they are eliminated by size discrimination based on light scatter.

In general, as can be readily glanced from Table 2, there is an unequivocal relationship between two dye concentrations in a given population of beads and location of said populations on X-Y map. Each location is assigned in terms of red (FL3) or orange (FL2) dyes intensity as expressed in linear fluorescence channels units which fall in approximately 470, 580, 690, 750, 800, 900, and 990 series. For practical reasons, i.e., space limitation in the bead cluster, the last digit "0" is omitted. The first two digits in each bead population represents fluorescence intensity of orange dye (FL2) and last two digits the intensity of the red dye (FL2). The fluorescent intensity increases as the numbers go higher. The beads with lowest intensity (4725) reside in lower left corner and brightest ones (9998) in upper right corner. As they move vertically up a column, both red and orange dye amounts in a bead must be increased. This is because there is a substantial amount of energy transfer from the orange dye to the red. When moving horizontally from left to right across a row, the red dye must be decreased in order to maintain a steady FL3 value. This is due to overlap of the orange dye spectrum into the red region, thus necessitating the increase in FL3 signal. In this manner multiple, non-overlapping populations of beads are constructed. Two parameters namely, a fluorescent color (red or orange) and color intensity or brightness (expressed in fluorescence channel units), are essential to classify obtained beads and are termed as a fluorescence signal.

Hence, particular populations of beads are provided whose fluorescence characteristics or signals fall within a prescribed region depicted in a Fluorescence Bead Map. Typically, about 80% or greater of the individual beads within a particular population of beads will exhibit fluorescence characteristics within the desired region, preferably about 90% or greater, more preferably about 97% or greater, most preferably about 99% or greater. For each set of beads, typically about 1% or less of the individual beads within a particular set of beads will exhibit fluorescence characteristics that fall within another, undesired region, preferably about 0.5% or less, more preferably about 0.3% or less, most preferably about 0.2% or less.

While theoretically any number of populations or subsets can be present in each Bead Map, due to the limitations in the prior art techniques it is not possible to obtain more than 6 subsets coexisting simultaneously. While theoretically it has been speculated that such subsets can be extremely valuable for multiplex analysis (see for example McHugh, "Flow Microsphere Immunoassay for the Quantitative and Simultaneous Detection of Multiple Soluble Analytes," in Methods in Cell Biology, 42, Part B, (Academic Press, 1994) so far there are no known examples in the art enabling and demonstrating the reduction to practice of tangible, multicolored beads. At best only 1 and perhaps a maximum of 5 population of beads containing various ratios of two dyes could have been possible. For example, U.S. Pat. No. 4,717,655 discloses such beads, however, the disclosure was not enabled and the method of incorporating dyes in these beads is by copolymerization process and as such it is unrelated to the instant invention. In contrast, due to a significant improvement over existing methodology it is now technically possible to obtain 16-subset, 32-subset, 64-subset or even higher number of bead collections using the instant methodology.

As an example 64-subset bead collection or 64 populations of beads were constructed each population differing from another by a distinct location on the X-Y plot. These locations essentially do not overlap. As opposed to the prior art methods which result in up to 10-20% or even higher rate of dispersion the instant method allows to obtain essentially homogeneous populations of beads with only 0.2-0.3% dispersion. As used hereinafter the term essentially non-overlaping populations means that only about 0.2-0.3% of beads in each population may display an optical pattern or fluorescent signal which can be ascribed to the neighboring cluster of beads having the same set of fluorescent dyes but mixed at different ratio. This is a significant improvement over the prior art.

EXAMPLE 3

Although multiplexed analysis capability theoretically would provide enormous benefit in the art of flow cytometry, very little progress has been previously achieved due to technical limitations in obtaining sufficient variety of multicolored, non-overlaping subsets of fluorescent beads. A review of some of these prior art techniques is provided by McHugh (see above). These methods have been unsatisfactory as applied to provide fully multiplexed assay capable of analysis of more than a few different analytes. In the prior art when beads were incorporating a combination of 2 dyes only 5 subsets of beads were allegedly obtained (U.S. Pat. No. 4,717, 655 issued to Fulwyler). A set with maximum of six subsets is obtained using Bangs method (see Example 1) which is still insufficient for the purposes of truly multiplexed assay.

A series of antibodies, antigens, or nucleic acid probes, collectively named hereinafter as analytical reactants, are attached to the beads by any of a number of conventional procedures such as by chemical or physical adsorption as described by Colvin et al., "The Covalent Binding of Enzymes and Immunoglobulins to Hydrophilic Microspheres" in Microspheres: Medical and Biological Applications, 1-13, CRC, Boca Raton, Fla., 1988; Cantarero et al., "The Adsorptive Characteristics of Proteins for Polystyrene and Their Significance in Solid-Phase Immunoassays," Anal Biochem, 105, 375-382 (1980); and Illum et al., "Attachment of Monoclonal Antibodies to Microspheres," Methods in Enzymol, 112, 67-84 (1985) 112, 67-84 (1985).

After attachment of a reactant to the beads' surface, aliquots from each subset are mixed to create a pool containing known amounts of beads within each subset. Preferably, the pooled set is prepared with equal volumes of beads from each subset, so that the set contains about the same number of beads from each subset or population. This pool is then be incubated with a fluid sample of interest, such as serum or plasma, to test for the presence of antibodies in the fluid that are reactive with antigens on the beads. Such incubation is generally performed under conditions of temperature, pH, ionic concentrations, and the like that facilitate specific reaction of antibodies in the fluid sample with antigen on the bead surface. After a sufficient period of time, the beads in the mixture are centrifuged, washed and incubated for another period of time with a "secondary" antibody such as, for example, fluorescein labeled goat anti human immunoglobulin. The secondary antibody or label reagent will bind to and fluorescently label antibodies bound to antigen on the beads. After washing (or without washing), the beads are processed by a flow cytometer and the four classification parameters forward light scatter, side light scatter, red fluorescence, and orange fluorescence are measured and used to identify the subset or population to which each bead belongs. A simultaneous measurement of green fluorescence (measurement parameter) for each bead allows one to determine whether the bead has antibody bound to it. Because the subset to which a bead belongs is correlated with the presence of a particular antigen, e.g., series of grass allergens, various substance abuse drugs, one may readily determine the specificity of the antibody bound to a bead as a function of the subset to which it belongs.

Displacement or Competition Assay

Assays for many substances in a clinical laboratory are based on the interference with specific ligand-ligate or antigen-antibody interactions. In these assays, one member of the ligand-ligate pair is labeled with the fluorophore or fluorochrome and one member is immobilized on the beads. Soluble, unlabeled analyte, which may be ligand or ligate, is added to the reaction mixture to competitively inhibit interaction of the labeled component with the immobilized component. It is usually not important which member of the pair is labeled and which is immobilized; however, in certain assays, functional advantages may dictate the orientation of the assay. In an exemplary assay of this type, each bead subset is provided with an antigen. The antigen-coated beads are then reacted with labeled antibody specific for the antigen on the bead surface. Subsequent addition of a test fluid containing soluble analyte (inhibitor) will displace the labeled antibody from the beads in direct proportion to the concentration of the soluble analyte. A standard curve of known analyte concentrations is used to provide accurate quantification of analyte in the test sample.

Nucleic Acid Analysis

The power and sensitivity of PCR found its application to a wide variety of analytical problems in which detection of DNA or RNA oligonucleotide sequences is required. One major difficulty with the PCR technique is the cumbersome nature of the methods of measuring end-product, i.e., amplified DNA. A flow cytometric bead-based hybridization assay permits the extremely rapid and accurate detection of genetic sequences of interest. In a preferred embodiment of this invention, a bead to which a nucleic acid segment of interest has been coupled is provided. A PCR product of interest (or any other DNA or cDNA segment) is detected by virtue of its ability to competitively inhibit hybridization between the nucleic acid segment on the bead and a complementary fluorescent DNA probe. The method is sensitive and precise and allows the detection of single point mutations in the PCR product or DNA of interest. The multiplexed DNA analysis method can be applied to detect any PCR product or other DNA of interest for specific polymorphisms or mutations and one skilled in the art will recognize that numerous applications can be imagined such as presence of histocompatibility alleles associated with susceptibility to diseases, mutations associated with genetic diseases, autoimmune diseases, or mutations of oncogenes associated with neoplasia or risk of neoplasia. In a same way nucleic acid segments from pathogenic organisms such as bacterial, viral, fungal, mycoplasmal, rickettsial, chlamydial, or protozoan pathogens can be detected simultaneously.

Enzyme Assays

The invention is also useful for measurement of enzymes, enzyme inhibitors and other analytes. For example, bead subsets are generated with selected fluorescent substrates which are enzymatically cleaved from the bead, resulting in a loss of fluorescence. Enzymes that can be detected and measured using the invention include but are not restricted to, proteases, glycosidases, nucleotidases, and oxidoreductases. Any enzyme that results in selected bond cleavage can be measured. Alternatively, the action of the enzyme on the bead-bound substrate results in the formation or identification of a ligate for a fluorescent ligand present in the reaction mixture. The bead bearing the modified substrate then becomes fluorescent by virtue of binding of the fluorescent ligand to the newly formed ligate. Because each type of bead bearing the unique substrate can be distinguished, a mixture of bead subsets can be used to measure several enzyme activities simultaneously in the same reaction mixture.

Fluids or samples with analytes that can be analyzed using these techniques include plasma, serum, tears, mucus, saliva, urine, pleural fluid, spinal fluid and gastric fluid, sweat, semen, vaginal secretions, fluid from ulcers and other surface eruptions, blisters, and abscesses, and extracts of tissues including biopsies of normal, malignant, and suspect tissues.

The above examples can be used to perform most common immunodiagnostic and nucleic acid assays. Other applications such as high throughput screening of combinatorial chemistry libraries for discovering new drugs, environmental screening of pollutants, drug testing, food safety-related investigations, testing of multiple analytes for agricultural needs, etc, can be imagined.

It is to be understood that, while the foregoing invention has been described in detail by way of illustration and example of preferred embodiments, numerous modifications, substitutions, and alterations are possible without departing from the spirit and scope of the invention as described in the following claims.

TABLE 1

| Sample | FL2 (CV) | FL3 (CV) | Events |
| --- | --- | --- | --- |
| Old Method | | | |
| A | 24.2 | 25.9 | 10000 |
| B | 27.7 | 25.5 | 10000 |
| C | 27.7 | 23.2 | 10000 |
| Improved Method | | | |
| A | 7.3 | 6.8 | 10000 |
| B | 7.3 | 6.7 | 10000 |
| C | 7.2 | 6.7 | 10000 |

TABLE 2

| | FL3 Red Dye (mM) | FL2 Orange Dye (mM) |
| --- | --- | --- |
| Region 47 series | | |
| 470/250 | 0.0495 | 0.00441 |
| 470/340 | 0.104 | 0.0041 |
| 470/415 | 0.0685 | 0.004 |
| 470/470 | 0.388 | 0.00576 |
| 470/525 | 0.458 | 0.0039 |
| 470/580 | 0.981 | 0.00662 |
| 470/635 | 0.132 | 0.00557 |
| 470/690 | 1.831 | 0.00637 |
| 470/745 | 3.84 | 0.01138 |
| 470/810 | 11.29 | 0.0278 |
| Region 58-series | | |
| 580/250 | 0.0201 | 0.00994 |
| 580/340 | 0.0582 | 0.00979 |
| 580/415 | 0.0763 | 0.00161 |

TABLE 2-continued

| | FL3 Red Dye (mM) | FL2 Orange Dye (mM) |
|---|---|---|
| 580/470 | 1.38 | 0.0256 |
| 580/525 | 0.42 | 0.0114 |
| 580/580 | 0.613 | 0.0162 |
| 580/635 | 1.15 | 0.0132 |
| 580/690 | 2.71 | 0.0267 |
| 580/745 | 0.643 | 0.0248 |
| 580/810 | 7.5 | 0.0489 |
| 580/870 | 9.71 | 0.008 |
| Region 69-series | | |
| 690/360 | 0.048 | 0.024 |
| 690/415 | 0.129 | 0.024 |
| 690/470 | 0.226 | 0.023 |
| 690/525 | 0.45 | 0.029 |
| 690/580 | 0.89 | 0.0459 |
| 690/635 | 1.11 | 0.0322 |
| 690/690 | 2.45 | 0.07 |
| 690/745 | 2.88 | 0.0624 |
| 690/810 | 5.54 | 0.185 |
| 690/870 | 5.68 | 0.145 |
| 750/940 | 10.52 | 1.07 |
| Region 80-series | | |
| 800/415 | 0.0465 | 0.15 |
| 800/470 | 0.123 | 0.131 |
| 800/525 | 0.226 | 0.061 |
| 800/580 | 0.504 | 0.0835 |
| 800/635 | 0.62 | 0.0805 |
| 800/690 | 1.18 | 0.118 |
| 800/745 | 1.7 | 0.113 |
| 800/800 | 3.06 | 0.218 |
| 800/870 | 5.7 | 0.31 |
| 800/940 | 7.54 | 0.806 |
| 950/940 | 7.93 | 0.736 |
| Region 90-series | | |
| 900/510 | 0.084 | 0.0017 |
| 900/553 | 0.0666 | 0.0146 |
| 900/596 | 0.138 | 0.0913 |
| 900/645 | 1.29 | 0.253 |
| 900/690 | 0.861 | 0.298 |
| 900/734 | 0.699 | 0.229 |
| 900/779 | 0.984 | 0.214 |
| 900/823 | 1.13 | 0.435 |
| 900/867 | 2.61 | 0.381 |
| 900/912 | 3.41 | 0.579 |
| 900/953 | 4.88 | 0.861 |
| Region 99-series | | |
| 990/600 | — | 0.274 |
| 990/640 | 0.125 | 0.21 |
| 990/680 | 0.21 | 0.268 |
| 990/720 | 0.472 | 0.216 |
| 990/760 | 0.712 | 0.275 |
| 990/800 | 0.82 | 0.278 |
| 990/840 | 1.12 | 0.446 |
| 990/880 | 1.87 | 0.431 |
| 990/920 | 3.24 | 0.477 |
| 990/980 | 2.93 | 0.763 |

What is claimed is:

1. A population of polymeric microspheres dyed with two or more fluorescent dyes, obtained by a method comprising:
treating polymeric microspheres by adding a polar organic solvent to an aqueous solution containing the polymeric microspheres to produce a mixture; and
adding at least two fluorescent dyes to the mixture such that the polymeric microspheres are stained with the at least two fluorescent dyes, wherein the at least two fluorescent dyes are selected such that on isolation and excitation of the polymeric microspheres, a distinct fluorescence signal is emitted from each dye, wherein the distinct fluorescence signals have an intensity proportional to the amount of the dye in the polymeric microspheres, and wherein the distinct fluorescence signals are substantially equivalent to targeted fluorescence signals that have been used to determine a concentration ratio of the at least two fluorescent dyes added to the mixture.

2. The population of claim 1, wherein the polar organic solvent is an aliphatic alcohol, methanol, ethanol, or propanol.

3. The population of claim 1, wherein the intensity exhibits a coefficient of variation among all of the polymeric microspheres that is no greater than about 15 percent.

4. The population of claim 1, wherein the intensity exhibits a coefficient of variation among all of the polymeric microspheres that is no greater than about 10 percent.

5. The population of claim 1, wherein the intensity exhibits a coefficient of variation among all of the polymeric microspheres that is no greater than about 8 percent.

6. The population of claim 1, wherein the at least two fluorescent dyes are hydrophobic.

7. The population of claim 1, wherein the at least two fluorescent dyes comprise squaric acid-based dyes.

8. The population of claim 7, wherein the squaric acid-based dyes are cyclobutenedione derivatives, symmetrical and unsymmetrical squaraines, substituted cephalosporin compounds, fluorinated squaraine compositions, alkylalkoxy squaraines, or squarylium compounds.

9. The population of claim 7, wherein the squaric acid-based dyes are a red fluorescent dye or an orange fluorescent dye.

10. The population of claim 9, wherein the red fluorescent dye comprises 1,3-bis[(1,3-dihydro-1,3,3-trimethyl-2H-indol-2-ylidene)methyl]-2,4-dihydroxycyclobutenediylium, bis(inner salt), and wherein the orange fluorescent dye comprises 2-(3,5-dimethylpyrrol-2-yl)-4-(3,5-dimethyl-2H-pyrrol-2-ylidene)-3-hydroxy-2-cyclobuten-1-one.

11. The population of claim 1, wherein the polymeric microspheres comprise polystyrene, brominated polystyrene, polyacrylic acid, polyacrylonitrile, polyacrylamide, polyacrolein, polydimethylsiloxane, polybutadiene, polyisoprene, polyurethane, polyvinyl acetate, polyvinylchloride, polyvinylpyridine, polyvinylbenzylchloride, polyvinyltoluene, polyvinylidene chloride, polydivinylbenzene, polyglycidylmethacrylate, polymethylmethacrylate, or copolymers, blends, composites, or combination thereof.

12. The population of claim 1, wherein the polymeric microspheres comprise at least one analytical reactant bound covalently to functional groups present on a surface of the polymeric microspheres or passively adsorbed to the surface of the polymeric microspheres.

13. The population of claim 1, wherein the polymeric microspheres have a diameter between about 10 nm and 100 µm.

14. A collection of distinct populations of polymeric microspheres according to claim 1, each population exhibiting an emission spectrum in a Fluorescence Bead Map, which is unique to said population.

15. The collection of claim 14, comprising eight or more distinct populations of the polymeric microspheres.

16. The collection of claim 14, comprising sixteen or more distinct populations of the polymeric microspheres.

17. The collection of claim 14, comprising twenty-four or more distinct populations of the polymeric microspheres.

18. The collection of claim 14, comprising thirty-two or more distinct populations of the polymeric microspheres.

19. The collection of claim 14, comprising sixty-four or more distinct populations of the polymeric microspheres.

20. The collection of claim 19, wherein there is substantially no overlap between any of the sixty-four or more emission spectra associated with the sixty-four or more distinct populations.

21. A set of distinct populations of polymeric microspheres dyed with at least two fluorescent dyes, wherein the set of distinct populations of polymeric microspheres is dyed using a method comprising:
   treating separate populations of polymeric microspheres by adding a polar organic solvent to aqueous solutions containing the separate populations of polymeric microspheres to produce different mixtures;
   preparing a series of solutions, each comprising at least two fluorescent dyes in a solvent, wherein each of the solutions in the series has a different concentration of at least one of the at least two fluorescent dyes; and
   adding said each of the solutions to one of the different mixtures to provide the set of distinct populations of polymeric microspheres, wherein each of the distinct populations of polymeric microspheres emits a different targeted fluorescence intensity from the at least one of the at least two fluorescent dyes upon excitation, and wherein the different targeted fluorescence intensities have been used to determine the different concentrations of the at least two fluorescent dyes included within each of the solutions.

22. The set of claim 21, wherein the polar organic solvent is an aliphatic alcohol, methanol, ethanol, or propanol.

23. The set of claim 21, wherein the different fluorescence intensity of said each of the distinct populations exhibits a coefficient of variation of no greater than about 15 percent.

24. The set of claim 21, wherein the different fluorescence intensity of said each of the distinct populations exhibits a coefficient of variation of no greater than about 10 percent.

25. The set of claim 21, wherein the different fluorescence intensity of said each of the distinct populations exhibits a coefficient of variation of less than about 8 percent.

26. The set of claim 21, wherein the at least two fluorescent dyes are hydrophobic.

27. The set of claim 26, wherein the at least two fluorescent dyes comprise squaric acid-based dyes.

28. The set of claim 27, wherein the squaric acid-based dyes comprise cyclobutenedione derivatives, symmetrical and unsymmetrical squaraines, substituted cephalosporin compounds, fluorinated squaraine compositions, alkylalkoxy squaraines, or squarylium compounds.

29. The set of claim 27, wherein the squaric acid-based dyes comprise a red fluorescent dye or an orange fluorescent dye.

30. The set of claim 29, wherein the red fluorescent dye comprises 1,3-bis[(1,3-dihydro-1,3,3-trimethyl2H-indol-2-ylidene)methyl]-2,4-dihydroxycyclobutenediylium, bis(inner salt), and wherein the orange fluorescent dye comprises 2(3,5-dimethylpyrrol-2-yl)-4-(3,5-dimethyl-2H-pyrrol-2-ylidene)-3-hydroxy-2-cyclobuten-1-one.

31. The set of claim 21, wherein the polymeric microspheres comprise polystyrene, brominated polystyrene, polyacrylic acid, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidene chloride, polydivinylbenzene, polyglycidylmethacrylate, polymethylmethacrylate, or copolymers, blends, composites, or combinations thereof.

32. The set of claim 21, wherein the polymeric microspheres comprise at least one analytical reactant bound covalently to functional groups present on a surface of the polymeric microspheres or passively adsorbed to the surface of the polymeric microspheres.

33. The set of claim 21, wherein the polymeric microspheres have a diameter between about 10 nm and 100 µm.

34. The set of claim 21, wherein said each of the distinct populations exhibits an emission spectrum in a Fluorescence Bead Map that is unique to said each of the distinct populations.

35. The set of claim 21, comprising eight or more of the distinct populations of polymeric microspheres.

36. The set of claim 21, comprising sixteen or more of the distinct populations of polymeric microspheres.

37. The set of claim 21, comprising twenty-four or more of the distinct populations of polymeric microspheres.

38. The set of claim 21, comprising thirty-two or more of the distinct populations of polymeric microspheres.

39. The set of claim 21, comprising sixty-four or more of the distinct populations of polymeric microspheres.

40. The set of claim 39, wherein said each of the distinct populations exhibits an emission spectrum in a Fluorescence Bead Map that is unique to said each of the distinct populations, and wherein there is substantially no overlap between any of the sixty-four or more emission spectra associated with the sixty-four or more of the distinct populations of polymeric microspheres.

41. A population of polymeric microspheres dyed with two or more fluorochromes, obtained by a method comprising:
   treating polymeric microspheres by adding a polar organic solvent to an aqueous solution containing the polymeric microspheres to produce a mixture; and
   adding at least two fluorochromes to the mixture such that the polymeric microspheres are stained with the at least two fluorochromes, wherein the at least two fluorochromes are selected such that on isolation and excitation of the polymeric microspheres, a distinct fluorescence signal is emitted from each fluorochrome, wherein the distinct fluorescence signals have an intensity proportional to the amount of the fluorochrome in the polymeric microspheres, and wherein the distinct fluorescence signals are substantially equivalent to targeted fluorescence signals that have been used to determine a concentration ratio of the at least two fluorochromes added to the mixture.

42. The population of claim 41, wherein the polar organic solvent is an aliphatic alcohol, methanol, ethanol, or propanol.

43. A set of distinct populations of polymeric microspheres dyed with at least two fluorochromes, wherein the set of distinct populations of polymeric microspheres is dyed using a method comprising:
   treating separate populations of polymeric microspheres by adding a polar organic solvent to aqueous solutions containing the separate populations of polymeric microspheres to produce different mixtures;
   preparing a series of solutions, each comprising at least two fluorochromes in a solvent, wherein each of the solutions in the series has a different concentration of at least one of the at least two fluorochromes; and
   adding said each of the solutions to one of the different mixtures to provide the set of distinct populations of polymeric microspheres, wherein each of the distinct populations of polymeric microspheres emits a different targeted fluorescence intensity from the at least two fluorochromes upon excitation, and wherein the different targeted fluorescence intensities have been used to determine the different concentrations of the at least two fluorochromes included within each of the solutions.

44. The set of claim 43, wherein the polar organic solvent is an aliphatic alcohol, methanol, ethanol, or propanol.

45. The set of claim 43, wherein the different fluorescence intensity of said each of the distinct populations exhibits a coefficient of variation of no greater than about 15 percent.

46. The set of claim 43, wherein the different fluorescence intensity of said each of the distinct populations exhibits a coefficient of variation of no greater than about 10 percent.

47. The set of claim 43, wherein the different fluorescence intensity of said each of the distinct populations exhibits a coefficient of variation of no greater than about 8 percent.

48. The set of claim 43, wherein at least one of the at least two fluorochromes is hydrophobic.

49. The set of claim 43, wherein the at least two fluorochromes are selected from fluorochromes that emit a red colored signal and fluorochromes that emit an orange colored signal.

50. The set of claim 43, wherein the polymeric microspheres comprise polystyrene, brominated polystyrene, polyacrylic acid, polyacrylonitrile, polyacrylamide, polyacrolein, polydimethylsiloxane, polybutadiene, polyisoprene, polyurethane, polyvinylacetate, polyvinylchloride, polyvinylpyridine, polyvinylbenzylchloride, polyvinyltoluene, polyvinylidene chloride, polydivinylbenzene, polyglycidylmethacrylate, polymethylmethacrylate, or copolymers, blends, composites, or combinations thereof.

51. The set of claim 43, wherein the polymeric microspheres comprise at least one analytical reactant bound covalently to functional groups present on a surface of the polymeric microspheres or passively adsorbed to the surface of the polymeric microspheres.

52. The set of claim 43, wherein the polymeric microspheres have a diameter between about 10 nm and 100 µm.

* * * * *